United States Patent
Sato

(10) Patent No.: US 8,064,572 B2
(45) Date of Patent: Nov. 22, 2011

(54) RADIATION IMAGING APPARATUS

(75) Inventor: Masaru Sato, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 206 days.

(21) Appl. No.: 12/588,385

(22) Filed: Oct. 14, 2009

(65) Prior Publication Data
US 2010/0091949 A1    Apr. 15, 2010

(30) Foreign Application Priority Data

Oct. 15, 2008  (JP) ................ 2008-266067

(51) Int. Cl.
*G01N 23/04* (2006.01)
*G01N 23/083* (2006.01)
(52) U.S. Cl. .......................... 378/62; 378/206
(58) Field of Classification Search ........ 378/51, 378/62, 162, 163, 165, 166, 204–206, 210
See application file for complete search history.

(56) References Cited

U.S. PATENT DOCUMENTS

| | | | |
|---|---|---|---|
| 5,933,472 A * | 8/1999 | Molz et al. ................... | 378/26 |
| 6,268,614 B1 | 7/2001 | Imai | |
| 2004/0105526 A1 * | 6/2004 | Zhang et al. ................ | 378/205 |
| 2009/0238341 A1 * | 9/2009 | Kawamura et al. .......... | 378/162 |
| 2009/0245464 A1 * | 10/2009 | Yamaguchi .................. | 378/62 |

FOREIGN PATENT DOCUMENTS

| | | |
|---|---|---|
| JP | 2005-270277 | 10/2005 |
| JP | 2008-023015 | 2/2008 |

* cited by examiner

*Primary Examiner* — Anastasia Midkiff
(74) *Attorney, Agent, or Firm* — Jean C. Edwards, Esq.; Edwards Neils PLLC

(57) ABSTRACT

The accuracy of combining positions of elongated images is improved at low cost, in a radiation imaging apparatus for generating elongated images having dimensions greater than a detectable range of a radiation image detecting means. A laser source is utilized. Displacement measuring means for measuring distances to targets by receiving a laser beam reflected by the subjects is provided. Positions that correspond to the ends of images in the movement direction of the radiation image detecting means are scanned in the direction perpendicular to the movement direction with the laser beam at each imaging operation. The displacement measuring means measures the positions of the ends of subjects in the laser scanning direction by receiving the laser beam reflected during scanning. An image processing means matches the combining positions of radiation images such that the ends of the subjects measured during each imaging operation are matched, and generates the elongated image.

2 Claims, 3 Drawing Sheets

RADIATION IMAGING APPARATUS

CROSS-REFERENCE TO RELATED APPLICATIONS

The present application claims priority from Japanese Patent Application No. 2008-266067, filed Oct. 15, 2008, the contents of which are herein incorporated by reference in their entirety.

BACKGROUND OF THE INVENTION

1. Field of the Invention

The present invention is related to a radiation imaging apparatus which is capable of obtaining elongated images having dimensions greater than a detectable range of a radiation image detecting means thereof.

2. Description of the Related Art

Conventionally, various radiation detectors, for obtaining radiation images to be utilized for medical diagnoses and the like, have been proposed and are in practical use.

For example, there are radiation detectors that utilize semiconductors such as amorphous selenium that generate electrical charges when irradiated by radiation, as disclosed in U.S. Pat. No. 6,268,614. Radiation detectors of this type that employ the so called optical readout method and the TFT readout method have been proposed. If these radiation detectors are employed, image information obtained by imaging operations can be obtained as digital data. This improves compatibility with diagnostic assisting devices and the like that employ computers.

In addition, Japanese Unexamined Patent Publication No. 2005-270277 proposes a method for generating an elongated image having dimensions greater than the detectable range of a radiation detector. In this method, the radiation detector is moved in a direction along and parallel to a radiation detecting surface of the radiation detector, and a plurality of imaging operations are performed at different positions. A plurality of images which are obtained by each imaging operation are combined, to generate the elongated image.

Further, Japanese Unexamined Patent Publication No. 2008-023015 discloses a radiation imaging apparatus equipped with a laser emitting means. The laser emitting means is utilized to display a cruciform mark on the surface of the body of a subject, to accurately determine the portion of the subject to be imaged during radiation imaging.

In the case that an elongated image is obtained by imaging a plurality of portions of a subject by moving a radiation detector and then combining the obtained images, the time of imaging differs for each image. Therefore, there is a problem that it becomes difficult to combine the images appropriately if the subject moves between imaging operations.

In order to solve this problem, it is desirable to obtain the position of the subject's body at each imaging operation, and to adjust the combining positions of the images when they are combined, based on the obtained positions. However, if a separate means for obtaining the position of subjects is provided, the construction of a radiation imaging apparatus becomes complex, and the cost thereof will increase.

Accordingly, there is demand for a radiation imaging apparatus that can solve the above problem at low cost.

The present invention has been developed in view of the foregoing circumstances. It is an object of the present invention to provide a radiation imaging apparatus for performing elongated imaging at dimensions greater than a detectable range of a radiation image detecting means, in which the accuracy of combining positions of elongated images is improved at low cost.

A radiation imaging apparatus of the present invention is a radiation imaging apparatus that moves a radiation image detecting means that obtains images of subjects by receiving irradiation of radiation which has passed through the subject with respect to the subjects to obtain a plurality of images at different positions, and combines the plurality of obtained radiation images to obtain elongated images having greater dimensions than the detectable range of the radiation image detecting means, comprising:

a radiation source for irradiating radiation;

a laser source for emitting a laser beam;

displacement measuring means, for measuring distances to a measurement target by receiving the laser beam which is reflected by the measurement target;

the radiation image detecting means;

moving means, for moving the radiation image detecting means in a direction along and parallel to a radiation detecting surface of the radiation image detecting means;

image processing means, for generating the elongated images by combining the plurality of radiation images; and control means, for controlling the laser source, the displacement measuring means, and the image processing means such that the laser source scans positions that correspond to the end portions of images in the movement direction of the radiation image detecting means in the direction perpendicular to the movement direction with the laser beam at each of a plurality of imaging operations, the displacement measuring means measures the positions of the end portions of the subjects in the scanning direction of the laser beam by receiving the laser beam which is reflected during the scanning, and the image processing means matches the combining positions of the radiation images such that the end portions of the subjects which are measured during each imaging operation are matched, to generate the elongated images.

Here, the "radiation image detecting means" may be a solid state detector that converts radiation to electric charges either directly or after converting the radiation to light, then outputs the electric charges to the exterior, to obtain image signals that represent radiation images of subjects.

The solid state detector may be of any of a variety of formats. Regarding a charge generating process for converting radiation to electrical charges, there are solid state detectors of a light conversion type, and solid state detectors of a direct conversion type, for example. A solid state detector of the light conversion type temporarily stores signal charges, obtained at a photoconductive layer by detecting fluorescence emitted by phosphors due to irradiation with radiation, in a charge accumulating section, then converts the accumulated charges to image signals (electrical signals) and outputs the image signals. The direct conversion type of solid state detector temporarily stores signal charges, generated within a photoconductive layer due to irradiation with radiation and collected by a charge collecting electrode, in a charge accumulating section, then converts the accumulated charges to electric signals and outputs the electric signals. Regarding a charge readout process for reading out the accumulated charges, there are an optical readout method and an electrical readout method. In the optical readout method, accumulated charges are read out by irradiating a solid state detector with readout light (electromagnetic waves for readout). In the electrical readout method, accumulated charges are read out by scanning TFT's (thin film transistors), a CCD (charge coupled device), or a CMOS (complementary metal oxide semiconductor) sensor, which are connected to a charge accumulating section. Further, the solid state detector may employ the improved direct conversion method disclosed in U.S. Pat. No. 6,268,614.

In the radiation imaging apparatus of the present invention, a configuration may be adopted, wherein:

the control means controls the radiation source, the laser source, the displacement measuring means, and the image processing means such that the laser source emits the laser beam toward the subjects at each of the plurality of imaging operations, the displacement measuring means measures the thickness of the subject by receiving the laser beam reflected by the subjects, and the radiation source adjusts the intensity of irradiated radiation during the imaging operations based on the thicknesses of the subjects, and/or the image processing means changes the contents of the image processes administered onto the radiation images.

Note that the measurement of the thicknesses of the subjects may be performed in the following manner. Because the distance from the laser source to an imaging stage of the apparatus is known (or measured when measuring the thickness of a subject), a subject may be caused to stand in front of the imaging stage, and the distance from the laser source to the subject may be measured. This measured distance may be subtracted from the aforementioned known distance, to measure the thickness of the subject.

According to the radiation imaging apparatus of the present invention, a laser source for displaying the cruciform mark, which the apparatus is already equipped with, is utilized to scan positions that correspond to the end portions of images in the movement direction of the radiation image detecting means in the direction perpendicular to the movement direction with the laser beam at each of a plurality of imaging operations, the positions of the end portions of the subjects in the scanning direction of the laser beam are measured by receiving the laser beam which is reflected during the scanning, and the image processing means matches the combining positions of the radiation images such that the end portions of the subjects which are measured during each imaging operation are matched, to generate the elongated images. Therefore, a low cost improvement of providing the displacement measuring means that measures distances to measurement targets by receiving laser beams reflected by the measurement targets enables improvement of the accuracy of combining positions for generating elongated images.

Note that the end portions of subjects can be detected by administering image analysis on the obtained radiation images. However, this configuration requires that the end portions of the subjects be pictured in the radiation images. In contrast, the present invention can improve the accuracy of the combining positions even in cases that the end portions of subjects are not pictured in the radiation images. Further, the necessity of image analysis is obviated, which enables processing times during combination of radiation images to be shortened.

A configuration may be adopted, wherein: the laser source emits the laser beam toward the subjects at each of the plurality of imaging operations, the displacement measuring means measures the thickness of the subject by receiving the laser beam reflected by the subjects, and the radiation source adjusts the intensity of irradiated radiation during the imaging operations based on the thicknesses of the subjects, and/or the image processing means changes the contents of the image processes (a contrast adjusting process and an outline emphasizing process, for example) administered onto the radiation images. In this case, it becomes possible to obtain elongated images having higher image quality.

DESCRIPTION OF THE PREFERRED EMBODIMENTS

Figure 1:
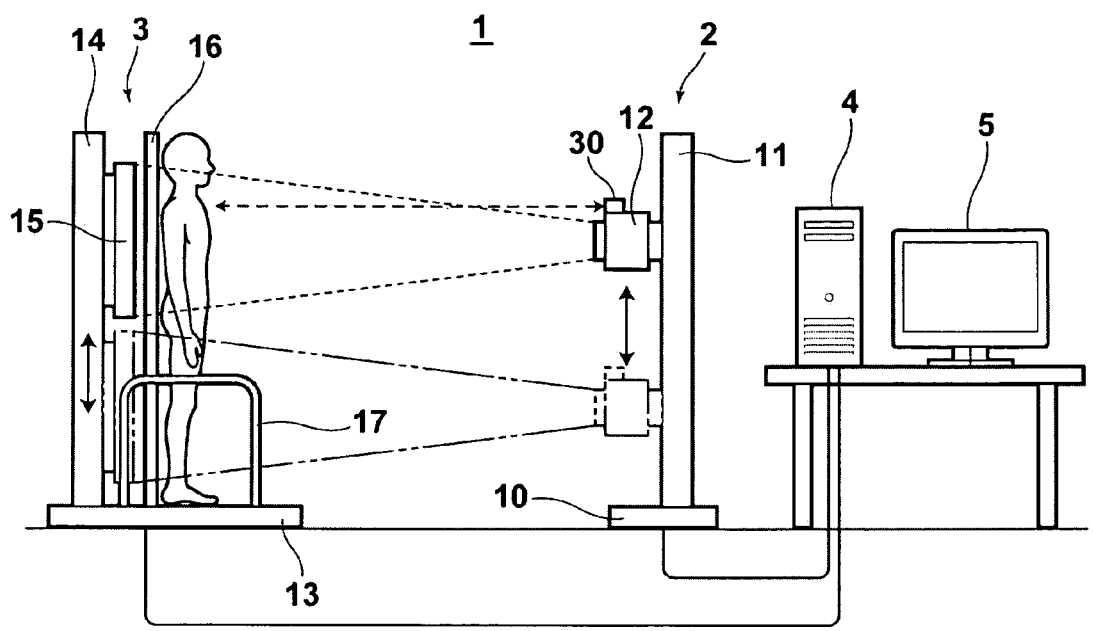
FIG. 1 is a side view that illustrates a radiation imaging system according to a preferred embodiment of the present invention.
Figure 2:
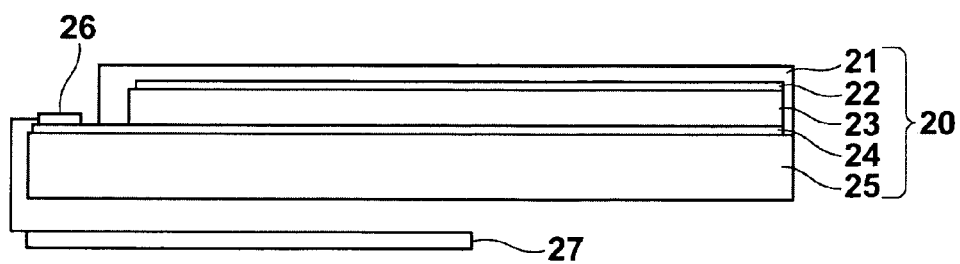
FIG. 2 is a schematic view that illustrates the construction of a solid state detector which is employed in a radiation imaging apparatus of the system of FIG. 1.

Hereinafter, an embodiment of the present invention will be described in detail with reference to the attached drawings. FIG. 1 is a side view that illustrates a radiation imaging system 1 according to a preferred embodiment of the present invention. FIG. 2 is a schematic view that illustrates the construction of a solid state detector which is employed in a radiation imaging apparatus of the system of FIG. 1.

The radiation imaging system 1 is constituted by: a radiation irradiating apparatus 2 equipped with a radiation source or the like; a radiation imaging apparatus 3 equipped with the solid state detector 20 for detecting radiation; a computer 4, which is connected to the radiation irradiating apparatus 2 and the radiation imaging apparatus 3; and a monitor 5 which is connected to the computer 4.

The radiation irradiating apparatus 2 is constituted by: a base 10; a support column 11 which is fixed on the base 10; and a radiation irradiating section 12 which has a radiation source housed therein. The radiation irradiating section 12 is mounted onto the support column 11 so as to be movable along the longitudinal direction thereof (the vertical direction in FIG. 1).

A laser unit 30 is equipped with: a laser source for emitting a laser beam; and a displacement measuring means that measures distances to measurement targets by receiving the laser beam reflected by the measurement targets. The laser unit 30 is capable of causing a cruciform mark for positioning to be displayed on the surfaces of the bodies of subjects during imaging operations. In addition, the laser unit is capable of scanning positions that correspond to the end portions of images in the movement direction of a radiation imaging section 15 to be described later in the direction perpendicular to the movement direction with the laser beam, measuring the positions of the end portions of the subjects in the scanning direction of the laser beam by receiving the laser beam which is reflected during the scanning, and measuring the thicknesses of imaged portions of the subjects.

In the radiation irradiating apparatus 2, the operations of the radiation source, the operations of the laser unit 30, the movement of the radiation irradiating section 12, and the like are controlled by a control means (not shown).

The radiation imaging apparatus 3 is constituted by: a base 13; a support column 14 which is fixed on the base 13; a radiation imaging section 15 which has the solid state detector 20 housed therein; a screen 16 to be placed between the radiation imaging section 15 and subjects; and hand rails 17 which are fixed on the base 13. The radiation imaging section 15 is mounted onto the support column 14 so as to be movable along the longitudinal direction thereof (the vertical direction in FIG. 1).

The radiation imaging system of the present embodiment is capable of performing two types of imaging operations, that include a standard imaging (a single imaging operation) and an elongated imaging (a plurality of imaging operations followed by image combination). The screen 16 is configured to be removable with respect to the base 13. In the case that elongated imaging is to be performed, the screen is mounted during the imaging operations, and in the case that elongated imaging is not to be performed, the screen is removed during the imaging operation. A sensor for detecting the mounted state of the screen 16 is provided on the base 13.

The solid state detector 20 is provided in the radiation imaging section 15 such that a radiation detecting surface thereof is parallel to the radiation incident surface of the radiation imaging section 15.

As illustrated in FIG. 2, the solid state detector 20 is constituted by: a glass substrate 25; a first conductive layer 24 formed by a-Si TFT's; a photoconductive layer 23 that generates electric charges and exhibits conductivity by receiving irradiation of radiation; a second conductive layer 22, and an insulating layer 21. The first conductive layer 24, the photoconductive layer 23, the second conductive layer 22, and the insulating layer 21 are formed on the glass substrate 25 in this order.

TFT's are formed in the first conductive layer 24 so as to correspond to each pixel. The output of each TFT is connected to an IC chip 26. The IC chip 26 is connected to an image signal processing section (not shown), which is printed on a printed circuit board 27.

The solid state detector 20 operates in the following manner. An electric field is formed between the first conductive layer 24 and the second conductive layer 22. If radiation is irradiated onto the photoconductive layer 23 at this time, charge pairs are generated within the photoconductive layer 23. Latent image charges corresponding to the amount of charge pairs are accumulated within the first conductive layer 24. When reading out the accumulated latent image charges, the TFT's of the first conductive layer 24 are sequentially driven to read out analog signals corresponding to the latent image charges corresponding to each pixel. The analog signals for each pixel are detected by the image signal processing section, and composed in the arrangement order of the pixels. The composed analog signals are converted into digital image signals by an A/D converter (not shown). The generated digital image signals are output from the image signal processing section to the computer 4 via a memory.

In the radiation imaging apparatus 3, the operation of the solid state detector 20, the rotating operation of the cam 36, the movement of the radiation imaging section 15, and the like are controlled by the control means (not shown). Note that the control means also functions to notify the mounted state of the screen 16 with respect to the base 13 to the computer 4.

The computer 4 functions as the control means that controls the radiation irradiating apparatus 2 and the radiation imaging apparatus 3. In addition, the computer 4 functions to record and manage data regarding patients who are subjects of imaging, such as names and sex, and data regarding imaging operations, such as portions to be imaged, radiation dosages, and procedures.

Figure 3:
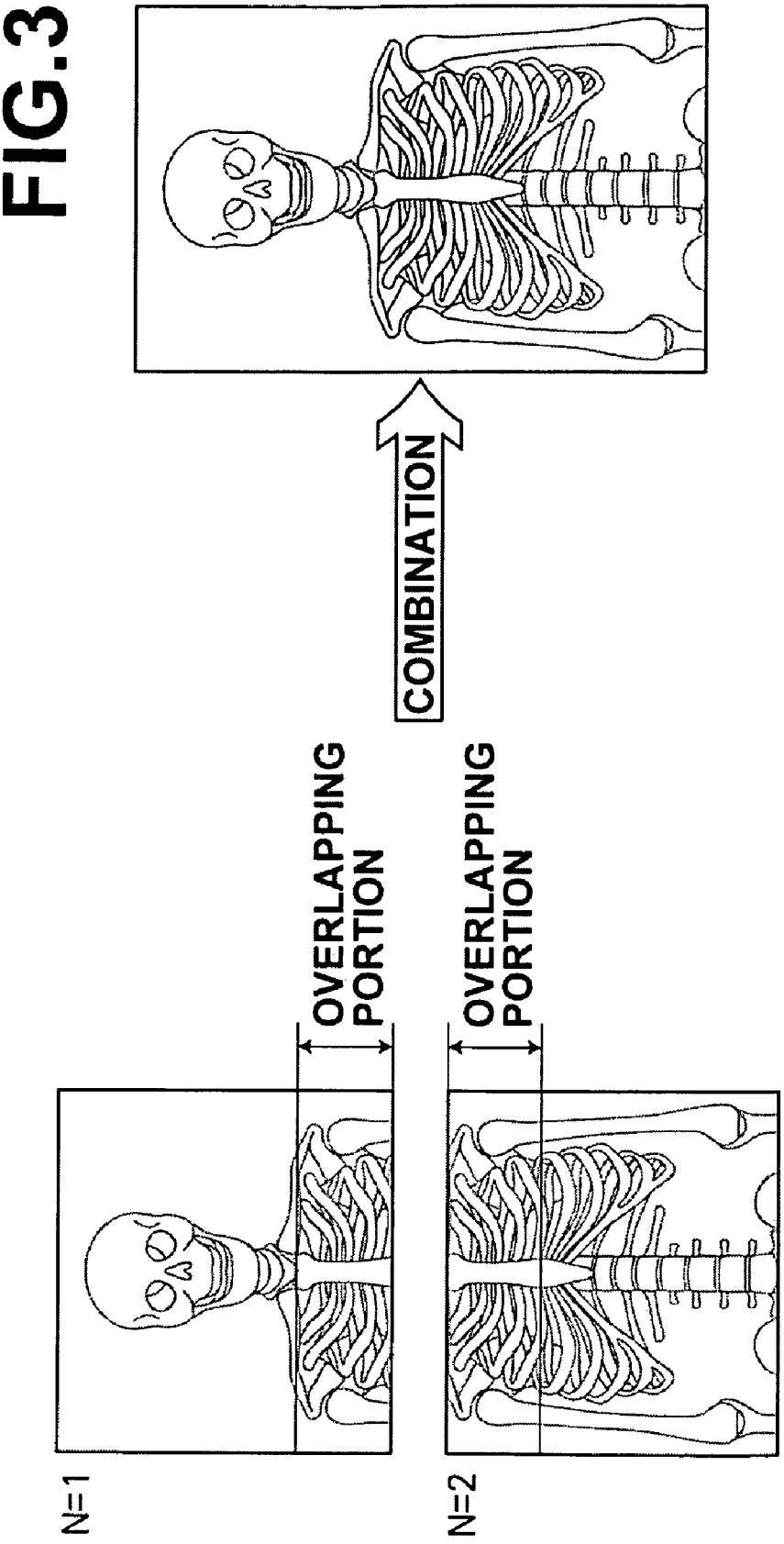
FIG. 3 is a diagram that illustrates an example of images which are obtained by the radiation imaging system of FIG. 1.
Figure 4:
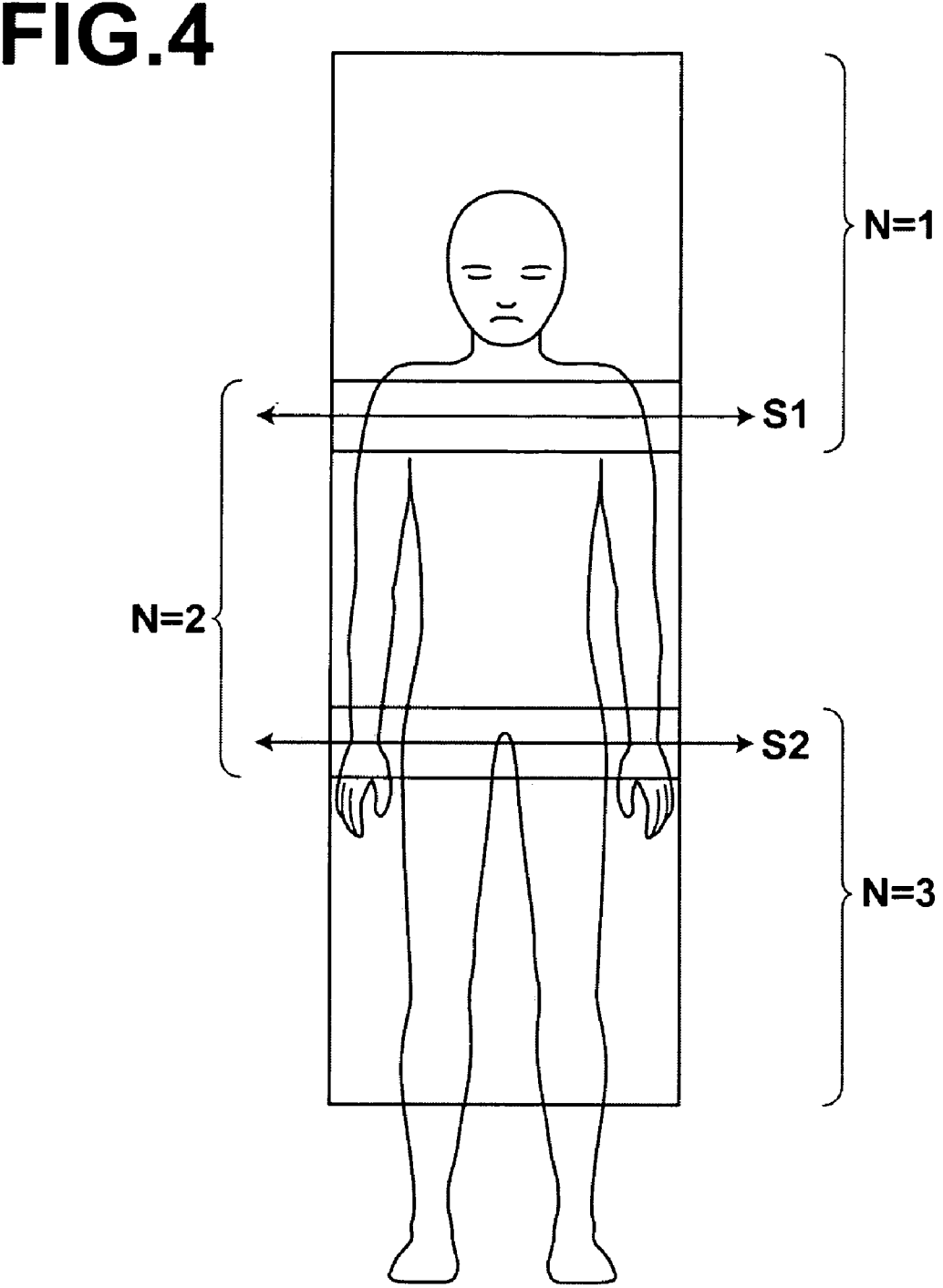
FIG. 4 is a diagram that illustrates the operation of the radiation imaging system of FIG. 1 during imaging operations.

Next, the operation of the radiation imaging system 1 having the above configuration will be described. FIG. 3 is a diagram that illustrates an example of an image which is obtained by the radiation imaging system 1. FIG. 4 is a diagram that illustrates the operation of the radiation imaging system 1 during imaging operations.

The radiation imaging system is capable of performing two types of imaging operations including standard imaging and elongated imaging. Here, a case in which elongated imaging is performed will be described.

In the case that elongated imaging is to be performed, an operator mounts the screen 16 onto the base 13. When the screen 16 is mounted onto the base 13, the radiation imaging apparatus 3 notifies the computer 4 of the mounted state.

When data indicating that the screen 16 has been mounted onto the base 13 is received from the radiation imaging apparatus 3, the computer 4 automatically switches the operating mode of the radiation imaging system 1 to an elongated imaging mode, and displays an elongated imaging menu on the monitor 5.

The operator causes a subject to stand at a position facing the screen 16. Then, the operator inputs a region, which is designated as an imaging range, to the computer 4. In the example illustrated n FIG. 4, a range from the head of a subject to the shins of the subject is set as the imaging range. Three imaging operations are performed to obtain images of the entirety of this range.

Thereafter, the intensity and irradiation time of radiation are specified and a two step radiation irradiation switch (not shown) is depressed halfway. At this time, the radiation irradiating section 12 and the radiation imaging section 15 are moved to a first imaging position. Then, the two step radiation irradiation switch is fully depressed, to initiate imaging. This two step switch is depressed until the entire imaging operation is completed. The system is configured such that irradiation of the radiation is immediately ceased in the case that depression of the switch is released during imaging.

When imaging is initiated, radiation is irradiated from the radiation irradiating section 12 toward the radiation imaging section 15, and a first imaging operation is performed.

At this time, positions that correspond to the ends of images in the movement direction of the radiation imaging section 15 are scanned in the direction perpendicular to the movement direction with the laser beam. The positions of the ends of subjects are measured in the laser scanning direction by receiving the laser beam reflected during scanning, and the measurement results are transmitted to the computer 4. Note that as illustrated in FIG. 4, an image obtained by the first imaging operation (a first image) is combined only with an image which is obtained by a second imaging operation (a second image). Therefore, only line Si, which is the borderline between the first image and the second image, needs to be scanned during the first imaging operation. Note that the measurement of the end portions may be performed either immediately prior to or immediately following irradiation of radiation, as long as the timing of the measurement is close to the irradiation of radiation.

Electric charges that bear radiation image information are accumulated as a latent image in the solid state detector 20 when radiation is irradiated thereon. The amount of accumulated latent image electric charges is approximately proportionate to the radiation dosage which has passed through the subject. Therefore, the latent image electric charges bear an electrostatic latent image of the subject.

After a predetermined amount of time elapses, recording onto the solid state detector 20 is ceased, to complete the imaging operation. Thereafter, the solid state detector 20 is caused to output analog signals corresponding to the latent image electric charges. The analog signals are converted into digital signals by the image signal processing section, to generate digital image signals N1. The generated digital image signals N1 are transmitted from the image signal processing section to the computer 4 via the memory.

When the digital image signals are received from the radiation imaging apparatus 3, the computer 4 causes a preview image of the digital image signals N1 to be displayed on the monitor 5, and the first imaging operation ends.

Thereafter, the radiation irradiating section 12 and the radiation imaging section 15 are moved downward, and a next imaging operation is performed. At this time, the radiation imaging section 15 is moved such that a portion of the previous imaging range is included (such that the images overlap). The radiation irradiating section 12 is also moved such that the images overlap. A second imaging operation and a third imaging operation are performed in the same manner as that of the first imaging operation, except for the scanning by the laser beam, to obtain digital image signals N2 and N3.

Regarding the scanning by the laser beam, as illustrated in FIG. 4, the image obtained by the second imaging operation (the second image) is combined with both the image obtained by the first imaging operation (the first image) and an image obtained by the third imaging operation (a third image). Therefore, during the second imaging operation, the line S1, which is the borderline between the first image and the second image, and a line S2, which is the borderline between the second image and the third image, needs to be scanned during the second imaging operation, to measure the end portions of the subject along both lines.

In addition, as illustrated in FIG. 4, the image obtained by the third imaging operation (the third image) is combined only with the image which is obtained by the second imaging operation (the second image). Therefore, only the line S2, which is the borderline between the second image and the third image, needs to be scanned during the third imaging operation.

Combining of the images obtained in the manner described above is performed by processing the overlapping portions of adjacent images by an averaging process. Note that the combining process is not limited to the averaging process, and any other process, such as a weighted averaging process, may be employed.

At this time, the combining positions for adjacent images may be adjusted such that the end portions of the subject which were measured during each imaging operation match in the horizontal direction in FIG. 3. For example, in the case that the position of the subject is shifted to the right by 2 mm during the second imaging operation with respect to the position of the subject during the first imaging operation, the first image and the second image may be combined such that the second image is shifted to the left 2 mm with respect to the first image.

In addition, with regard to the vertical direction in FIG. 3, pattern matching may be performed for each line, and the images may be combined at the location at which correlation is highest. The pattern matching process may be performed in a region of approximately the same range as the movement accuracy of the moving means for moving the radiation imaging section 15.

By adopting the configuration described above, a low cost improvement of providing the displacement measuring means that measures distances to measurement targets by receiving laser beams reflected by the measurement targets utilizing the laser source for displaying the cruciform mark, which the apparatus is already equipped with, enables improvement of the accuracy of combining positions for generating elongated images.

A preferred embodiment of the present invention has been described above. However, the present invention is not limited to the above embodiment, and various changes and modifications are possible. For example, a configuration may be adopted, wherein: the laser source emits the laser beam toward the subjects at each of the plurality of imaging operations, the displacement measuring means measures the thickness of the subject by receiving the laser beam reflected by the subjects, and the radiation source adjusts the intensity of irradiated radiation during the imaging operations based on the thicknesses of the subjects, and/or the image processing means changes the contents of the image processes (a contrast adjusting process and an outline emphasizing process, for example) administered onto the radiation images. In this case, it becomes possible to obtain elongated images having higher image quality. Note that the thicknesses of subjects may be those measured at the central portions of images, or an average value of thicknesses measured at a plurality of points within images.

In addition, the radiation irradiating section is not limited to that which moves unidirectionally as described above. Alternatively, the height of the radiation irradiating section may be fixed, and the radiation irradiating section may be configured to change only the irradiating direction of radiation.

Further, a solid state detector of the TFT readout type is utilized in the embodiment described above. Alternatively, a solid state detector of the optical readout type or other types of solid state detectors may be employed.

What is claimed is:

1. A radiation imaging apparatus that moves a radiation image detecting means that obtains images of subjects by receiving irradiation of radiation which has passed through the subject with respect to the subjects to obtain a plurality of images at different positions, and combines the plurality of obtained radiation images to obtain elongated images having greater dimensions than the detectable range of the radiation image detecting means, comprising:
   a radiation source for irradiating radiation;
   a laser source for emitting a laser beam;
   displacement measuring means, for measuring distances to a measurement target by receiving the laser beam which is reflected by the measurement target;
   the radiation image detecting means;
   moving means, for moving the radiation image detecting means in a direction along and parallel to a radiation detecting surface of the radiation image detecting means;
   image processing means, for generating the elongated images by combining the plurality of radiation images; and
   control means, for controlling the laser source, the displacement measuring means, and the image processing means such that the laser source scans positions that correspond to the end portions of images in the movement direction of the radiation image detecting means in the direction perpendicular to the movement direction with the laser beam at each of a plurality of imaging operations, the displacement measuring means measures the positions of the end portions of the subjects in the scanning direction of the laser beam by receiving the laser beam which is reflected during the scanning, and the image processing means matches the combining positions of the radiation images such that the end portions of the subjects which are measured during each imaging operation are matched, to generate the elongated images.

2. A radiation imaging apparatus as defined in claim 1, wherein:

the control means controls the radiation source, the laser source, the displacement measuring means, and the image processing means such that the laser source emits the laser beam toward the subjects at each of the plurality of imaging operations, the displacement measuring means measures the thickness of the subject by receiving the laser beam reflected by the subjects, and the radiation source adjusts the intensity of irradiated radiation during the imaging operations based on the thicknesses of the subjects, and/or the image processing means changes the contents of the image processes administered onto the radiation images.

* * * * *